United States Patent [19]

Giefer

[11] Patent Number: 4,585,488

[45] Date of Patent: Apr. 29, 1986

[54] METHOD FOR DISINFECTING CONTACT LENSES

[75] Inventor: Günter Giefer, Heusenstamm, Fed. Rep. of Germany

[73] Assignee: Ciba Vision Care Corporation, Atlanta, Ga.

[21] Appl. No.: 451,562

[22] Filed: Dec. 20, 1982

[30] Foreign Application Priority Data

Dec. 21, 1981 [DE] Fed. Rep. of Germany ....... 3150638

[51] Int. Cl.$^4$ .................. A61L 2/18; G02C 13/00
[52] U.S. Cl. ..................................... 134/27; 134/42; 252/106; 252/174.12; 422/30; 435/27; 435/195; 435/264
[58] Field of Search ................... 422/30; 435/27, 174, 435/188, 192, 264, DIG. 810; 134/2.27, 42; 252/106, 95, 174.12

[56] References Cited

U.S. PATENT DOCUMENTS

| | | | |
|---|---|---|---|
| 2,956,994 | 10/1960 | Peterlein | 252/429 |
| 3,240,709 | 3/1966 | Rankin | 252/106 |
| 3,282,702 | 11/1966 | Schreiner | 99/54 |
| 3,594,330 | 7/1971 | Delbouille et al. | 252/429 |
| 3,700,761 | 10/1972 | O'Driscoll et al. | 351/160 |
| 3,912,451 | 10/1975 | Gaglia | 134/42 |
| 4,013,410 | 3/1977 | Thomas et al. | 422/30 |
| 4,096,870 | 6/1978 | Manfuso, Jr. | 134/42 |
| 4,101,380 | 7/1978 | Rubinstein et al. | 435/181 |
| 4,368,081 | 1/1983 | Hata et al. | 422/30 |
| 4,414,127 | 11/1983 | Fu | 259/95 |
| 4,473,550 | 9/1984 | Rosenbaum et al. | 424/94 |
| 4,521,375 | 6/1985 | Houlsby | 422/29 |

FOREIGN PATENT DOCUMENTS

50-36685 4/1975 Japan.
53-24093 4/1978 Japan.

OTHER PUBLICATIONS

Levine et al, "Disinfection of Hydrophilic Contact Lenses with Commercial Preparations of 3% and 6% Hydrogen Peroxide", *Dev. Indus. Microbiol.*, vol. 22, pp. 813–819 (1981).

Block, "Disinfection, Sterilization and Preservation", 2nd Ed. (1977) pp. 677–684.

Scott, "Oxidoreductases", in *Enzyme in Food Processing* (G. Reed, publisher) 2nd Ed., pp. 247–250 (1975) Acadamic Press.

Heins et al, "Aktivatoren und Katalysatoren für die Oxidation mit Wasserstoff Peroxid" (a bridged version of lecture Feb. 3, 1971) Translation.

Hans V. Euler, "Chemie der Enzyme", Part II, Section 3, Die Katalasen und die Enzyme der Oxydation und Reduktion, pp. 1–9, 30–32 (1934, J. F. Bergmann, Munich).

Chemical Abstracts, vol. 83, p. 401, No. 112,398f.

Chemical Abstracts, vol. 87, p. 334, No. 81,798n (Bhuyan et al).

Merck Index, 9th Edition (1976), pp. 242–243, "Catalase".

Bitonte et al, "Symposium on the Flexible Lens", C. V. Mosby Co., St. Louis (1972), pp. 207–210.

"Hydrogen Peroxide", by Schumb, Reinhold Pub. Corp., N.Y. (1955) pp. 468, 486–488, 616.

"Soft Contact Lens", published by C. V. Mosby Co., St. Louis (1972) p. 247.

*Primary Examiner*—S. Leon Bashore
*Assistant Examiner*—K. M. Hastings
*Attorney, Agent, or Firm*—Brumbaugh, Graves, Donohue & Raymond

[57] ABSTRACT

A method for disinfecting and cleaning contact lenses is disclosed wherein the lenses are first treated with a peroxide solution to effect disinfection and then are subsequently treated with a catalyst which decomposes the peroxide in a rapid, turbulent manner so as to facilitate removal of surface contamination. The catalyst is preferably catalase, which when used as an aqueous solution is particularly effective in increasing the speed and thoroughness of peroxide removal from the lenses.

4 Claims, No Drawings

METHOD FOR DISINFECTING CONTACT LENSES

FIELD OF THE INVENTION

This invention relates to a method for disinfecting and cleaning hygienic particles, particularly contact lenses for the human eye, and more particularly to a method in which, during a first time interval, a hydrogen peroxide solution acts onto the hygienic article and, during a second time interval, residual hydrogen peroxide on the article is split into water and oxygen under the action of a catalyst.

BACKGROUND OF THE INVENTION

During the use of contact lenses, the lenses become contaminated and the accumulation of pathogenic germs must not be permitted to exceed a critical limit in order to avoid the danger of an infection of the eye. For this reason, a daily disinfection of contact lenses is necessary. This is primarily true for hydrophilic soft lenses, which are used widely today.

For this purpose, a method is known which utilizes hydrogen peroxide, which has both an oxidizing, germ-killing, cleaning effect and an odor-killing effect. In this method, the contact lenses are first exposed to the action of a 3 to 30 percent solution of hydrogen peroxide, which can for example take place in a small container in which the contact lenses are arranged in a carrying basket. The time period during which the hydrogen peroxide must act onto the contact lenses in order to achieve a sufficient disinfection and cleaning is approximately 20 minutes. The residual hydrogen peroxide which adheres to the contact lenses must subsequently be removed, and in the known method this is done by moving the contact lenses into a second container which contains a neutral liquid and a catalyst, in the presence of which catalyst the hydrogen peroxide is split up into water and oxygen according to the formula:

$$2 H_2O_2 \rightarrow 2 H_2O + O_2$$

The catalyst is a metal-coated solid body.

A disadvantage of the conventional method is that the second method step, namely the decomposition of the hydrogen peroxide, takes a relatively long time. At least four hours are typically needed for this. If, for example, a user of contact lenses forgets in the evening to change the contact lenses from the hydrogen peroxide solution to the solution containing the catalyst, there is usually insufficient time the next morning to remove the hydrogen peroxide residues from the contact lenses and thereby avoid a burning sensation in the eyes during wearing of the contact lenses. According to a modification of the known method, the metallic catalyst is already present in the hydrogen peroxide solution during the time when the hydrogen peroxide solution acts onto the contact lenses. Thus, the disinfecting and cleaning operation of the contact lenses and the decomposition of the hydrogen peroxide by the catalyst start at the same time. This is possible in the known method, since the decomposition which is effected by the catalyst takes place slowly. This one-step method also has the important disadvantage that it is very slow (it takes several hours). Moreover, in this known method, remaining residues of hydrogen peroxide are thereafter removed by a final washing of the lenses in a salt solution.

A basic purpose of the invention is to improve the method mentioned above so that the time span required for the second method step is substantially reduced and at the same time a very high-grade removal of the hydrogen peroxide is achieved.

The foregoing purpose is met by a method of the type set forth above in which the catalyst is catalase.

In one development of the invention, catalase is added, after the first time interval has elapsed, to the hydrogen peroxide solution in which the hygienic article is immersed.

In another development of the invention, the hydrogen peroxide solution is replaced with, or the hygienic article is moved to, a neutral liquid which contains catalase or to which catalase is subsequently added. The neutral liquid is preferably a sodium chloride solution. Catalase is added to the neutral liquid either in the form of tablets or in the form of a highly concentrated solution.

DETAILED DESCRIPTION

Catalase is an enzyme which is preferably obtained from beef liver and has a crystalline structure. It can be obtained on the market as a highly concentrated solution dissolved in 30% glycerin and 10% ethanol and is used in the grocery industry, in particular in the treatment of milk.

The invention is based on the recognition that the removal of hydrogen peroxide residues from the hygienic articles in the presence of catalase as catalyst take place substantially more quickly and thoroughly than when conventional catalysts are used. In the method according to the invention, the time span for the decomposition step takes only a few minutes (approximately 5 minutes). In the method according to the invention, it is thus not important if a user of contact lenses forgets in the evening to start the decomposition step, since taking care of it the next morning requires only a few minutes. Through the very turbulent decomposition of the hydrogen peroxide, not only is the necessary treatment time substantially shortened, but since the catalyst which is added in solution also reaches the hydrogen peroxide which has penetrated the contact lense material, an explosionlike decomposition takes place which breaks off contamination from the surface of the contact lenses, which contamination has become brittle during the first method step. The removal of hydrogen peroxide residues with the inventive method is so thorough that a subsequent washing of the lenses in a salt solution is not needed.

In using the organic material catalase, there exists a practical problem in that it is not very stable and storing it is difficult. The above-mentioned highly concentrated catalase solution, which can be obtained in commerce, must be stored at 4° C. and even then can be stored only for several months. According to the invention, the catalase for carying out the inventive method can be stored in sodium chloride solution, in which it has surprisingly been found to be capable of storage for a very long time with minimal temperature susceptibility. The stability of the catalase in this form makes the method according to the invention extremely well suited for practical use. For this purpose, a volume part of catalase in the above-mentioned commercially available form is added to approximately 100 to 1000 volume parts, preferably 400 to 600 volume parts, of an approximately 0.8 to 1.0% sodium chloride solution.

The decomposition step can be carried out in various ways. At the end of the disinfection time, catalase in the form of tablets or a highly concentrated solution can be added directly to the hydrogen peroxide in the treatment container. An alternative approach involves replacing the hydrogen peroxide solution in the container with a neutral liquid, for example a sodium chloride solution, to which is then added a somewhat highly concentrated catalase solution or tablets containing catalase. One can best use, as the liquid which replaces the hydrogen peroxide solution in the container, the above-mentioned liquid which consists of highly concentrated catalase stored in a sodium chloride solution. It is also possible to work with two containers, wherein one container contains the hydrogen peroxide solution and the other container contains the neutral liquid with the catalase. Particularly during the treatment of contact lenses, a sodium chloride solution is preferably used as the neutral liquid for the second method step, the concentration of which corresponds with the concentration of eye fluid (i.e. isotonic).

For practicality in carrying out the inventive method, it is also conceivable to press the catalase in a crystalline form, with a suitable highly water-soluble base material, into tablets. For the base material, commercially available substances can be used. These tablets then replace the above-mentioned highly concentrated catalase solution.

Other hygienic articles which can be treated according to the inventive method include, for example, dental protheses or the ear inserts of hearing aids.

The concentration in which the catalase is added, in its commercially available form, to the base liquid, for example the hydrogen peroxide solution or the sodium chloride solution, can vary in a wide range from approximately 0.1 to 1 percent by volume.

The embodiments of the invention in which an exclusive property or privilege is claimed are defined as follows:

1. A method for decomposing residual hydrogen peroxide adhering to a contact lens following sterilization of the lens with hydrogen peroxide and thereby rendering said lens suitable for wearing without any further sterilization or decomposition of hydrogen peroxide which comprises contacting said lens with an aqueous isotonic solution of dissolved catalase in an amount sufficient to decompose the residual hydrogen peroxide adhering to the lens.

2. A method according to claim 1 wherein said aqueous isotonic solution contains about 0.8 to 1.0% sodium chloride.

3. A method for disinfecting and cleaning a contact lens so that it is suitable for wearing without any further sterilization or decomposition of hydrogen peroxide which comprises contacting said lens with an aqueous solution of hydrogen peroxide to effect the sterilization thereof, then subsequently contacting said lens with an aqueous isotonic solution of dissolved catalase in an amount sufficient to decompose the residual peroxide adhering to said lens.

4. A method according to claim 3 wherein said aqueous isotonic solution contains about 0.8 to 1.0% sodium chloride.

* * * * *